(12) United States Patent
Tan et al.

(10) Patent No.: US 10,100,039 B2
(45) Date of Patent: Oct. 16, 2018

(54) ALLISARTAN ISOPROXIL POLYMORPH, ITS PREPARATION METHOD AND PHARMACEUTICAL

(71) Applicant: SHENZHEN SALUBRIS PHARMACEUTICALS CO., LTD, Shenzhen (CN)

(72) Inventors: Duanming Tan, Shenzhen (CN); Jun Ou, Shenzhen (CN)

(73) Assignee: SHENZHEN SALUBRIS PHARMACEUTICALS CO., LTD, Shenzhen (CN)

( * ) Notice: Subject to any disclaimer, the term of this patent is extended or adjusted under 35 U.S.C. 154(b) by 111 days.

(21) Appl. No.: 15/320,449

(22) PCT Filed: Jun. 5, 2015

(86) PCT No.: PCT/CN2015/080914
§ 371 (c)(1),
(2) Date: Dec. 20, 2016

(87) PCT Pub. No.: WO2015/192722
PCT Pub. Date: Dec. 23, 2015

(65) Prior Publication Data
US 2017/0152243 A1   Jun. 1, 2017

(30) Foreign Application Priority Data

Jun. 20, 2014  (CN) .......................... 2014 1 0281060

(51) Int. Cl.
*C07D 403/10*   (2006.01)
(52) U.S. Cl.
CPC ................. *C07D 403/10* (2013.01)

(58) Field of Classification Search
None
See application file for complete search history.

(56) References Cited

U.S. PATENT DOCUMENTS

| 8,178,569 B2* | 5/2012 | Guo ..................... C07D 403/10 514/381 |
|---|---|---|
| 2009/0036505 A1 | 2/2009 | Guo et al. |
| 2009/0326024 A1 | 12/2009 | Guo et al. |
| 2010/0168193 A1 | 7/2010 | Guo |
| 2010/0292286 A1 | 11/2010 | Guo et al. |

FOREIGN PATENT DOCUMENTS

| CN | 101195615 A | 6/2008 |
|---|---|---|
| CN | 103012377 A | 4/2013 |
| CN | 103965171 A | 8/2014 |
| WO | WO 2008067687 A1 | 6/2008 |
| WO | WO 2009049495 A1 | 4/2009 |
| WO | WO 2009146608 A1 | 12/2009 |

OTHER PUBLICATIONS

English Translation of the Written Opinion of the International Search Authority in corresponding PCT Application No. PCT/CN2015/080914, dated Sep. 11, 2015.
International Search Report in corresponding PCT Application No. PCT/CN2015/080914, dated Sep. 11, 2015.

* cited by examiner

*Primary Examiner* — Kamal A Saeed
(74) *Attorney, Agent, or Firm* — Leason Ellis LLP

(57) ABSTRACT

Disclosed are polymorph of allisartan isoproxil and a pharmaceutical composition thereof. The polymorph is non-electrostatic, highly flowable and highly stable, and can be used for treating hypertension and complications thereof.

11 Claims, 7 Drawing Sheets

ALLISARTAN ISOPROXIL POLYMORPH, ITS PREPARATION METHOD AND PHARMACEUTICAL

Figure 1:
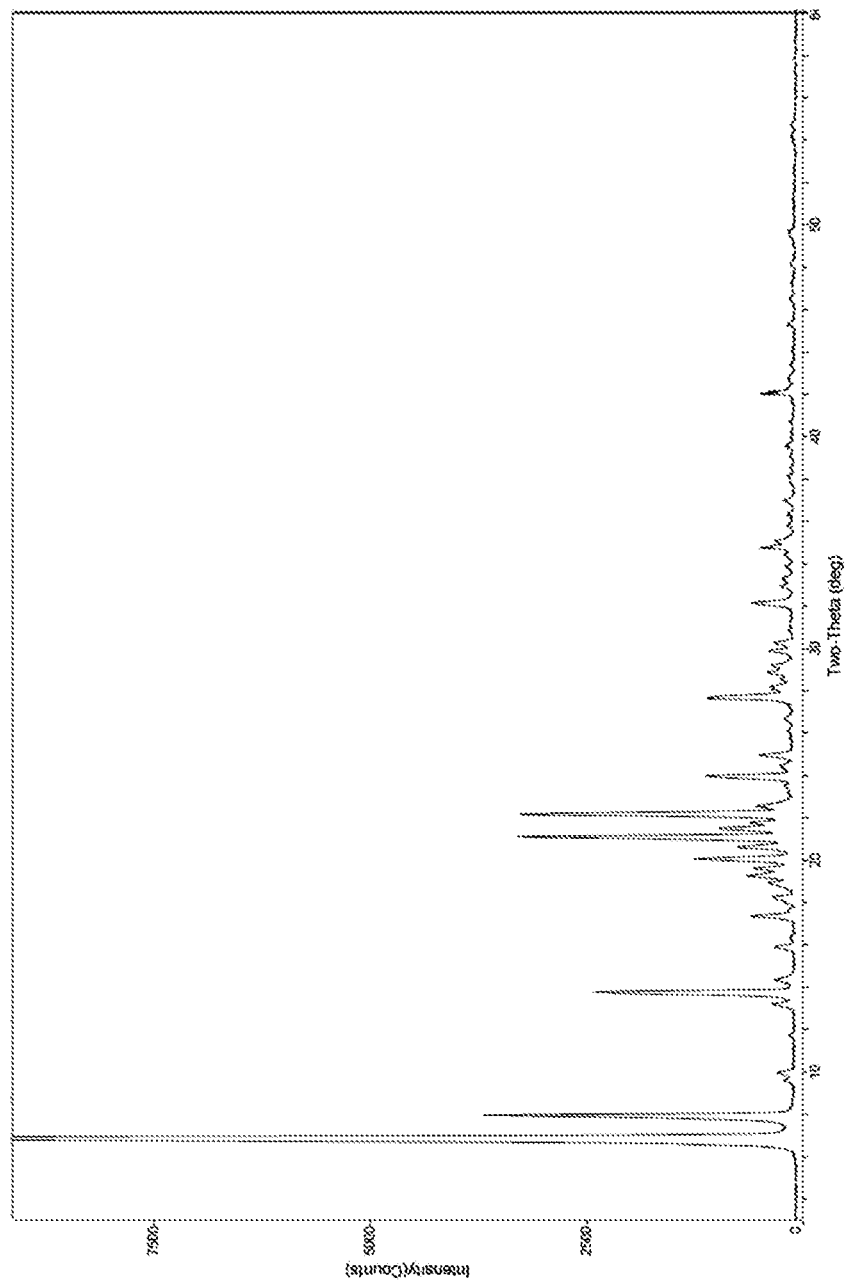

This application claims priority from a PCT patent application, application number PCT/CN2015/080914, Crystal of Allisartan Isoproxil, Preparation Method Therefore and Pharmaceutical Composition Containing Same, filed on 5 Jun. 2015, which claims priority from a Chinese utility patent application, application number 201410281060.5, Crystal of Allisartan Isoproxil, Preparation Method Therefore and Pharmaceutical Composition Containing Same, filed on 20 Jun. 2014, which are incorporated herein in their entireties by reference.

FIELD OF THE INVENTION

The present invention belongs to the field of pharmaceutical chemistry, in particular, it relates to an Allisartan isoproxil polymorph, its preparation method and pharmaceutical composition thereof.

BACKGROUND OF THE INVENTION

Allisartan isoproxil (CAS: 947331-05-7), with the chemical name: 2-butyl-4-chloro-1-[2'-(1H-tetrazol-5-yl)-1, 1'-biphenyl-methyl]-imidazole-5-carboxylic acid, 1-[(isopropoxy)-carbonyloxy]methyl ester, and the brand name: Xinlitan, is a new-type angiotensin II receptor antagonist. Chinese patent CN200610023991.0 firstly discloses its chemical structure and its application in the preparation of antihypertensive compositions. Compared with other antihypertensive products (such as losartan) of the same type, allisartan isoproxil shows advantages, such as low toxicity and excellent antihypertensive effect.

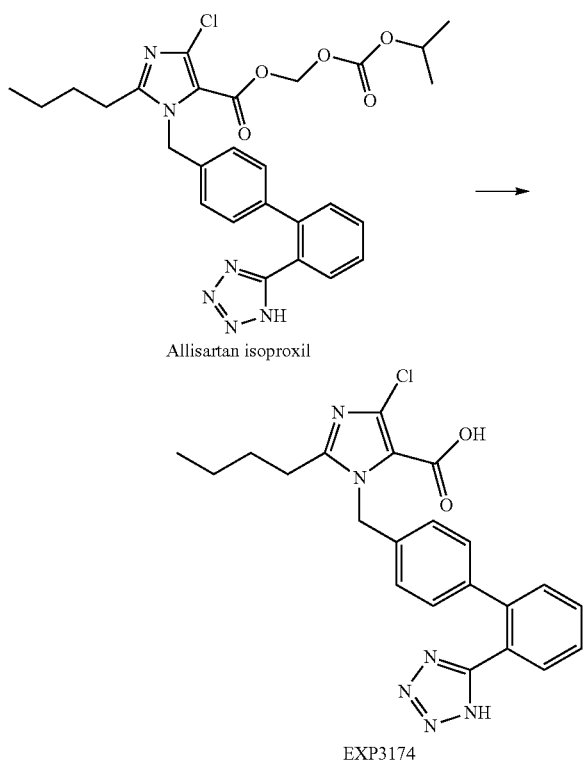

Study on polymorphism of drugs for superior polymorph is an important part in the process of drug research and also one of the important technologic steps for drug quality control. According to statistics, the vast majority of drugs are polymorphism, which directly affects the physicochemical properties (such as melting point, solubility, dissolution and stability) and clinical efficacy. Because specific polymorph is very unpredictable to be obtained, the physicochemical properties for different polymorphs of the same active ingredient are difficult to be predicted.

Chinese patent CN200710094131.0 discloses an allisartan isoproxil polymorph and its preparation method. This allisartan isoproxil polymorph is characterized by high stability, but with electrostatic phenomenon and poor flowability, even worse after grinding, easy to generate dust in the production process which causes contamination and also influences the feeding and blending in the following production process.

Chinese patents CN200710094021.4 and CN201110289695.6 separately disclose different preparation methods of allisartan isoproxil, the inventor repeats and finds that the polymorph of allisartan isoproxil obtained are consistent with that disclosed in Chinese patent CN200710094131.0.

In order to solve the shortcomings of available technologies, the inventor firstly tries to find a way to get an allisartan isoproxil crystal with non-electrostatic phenomenon, good flowability and high stability. By further research on the obtained crystal, the inventor is surprised to find that the obtained allisartan isoproxil crystal is a polymorph has not been disclosed, shows high stability, and meets the requirements of subsequent production. The new polymorph provides more options in raw materials for allisartan isoproxil preparation.

SUMMARY OF THE INVENTION

The first object of this invention is to overcome the shortcomings of available technologies, provide an allisartan isoproxil polymorph with non-electrostatic phenomenon, good flowability, high stability, etc.

Allisartan isoproxil polymorph mentioned in present invention has diffraction peaks at diffraction angles (2θ) of 6.9, 8.0, 13.8, 20.1, 21.1, 22.2, 24.0 and 27.7 in the X-ray powder diffraction spectra (XRD spectra) and the error range is ±0.2°. The relative intensity of mentioned peaks are stable at high value (5% and above), and these peaks which can appear stably in repeat tests, and can be classified as characteristic peaks of new polymorph in the present invention.

Allisartan isoproxil polymorph mentioned in the present invention has diffraction peaks at diffraction angle (2θ) of 17.4, 18.9, 19.3, 19.6, 21.5, 22.6, 32.1 and 34.8 in the X-ray powder diffraction spectra (XRD spectra) and the error range is ±0.2°. The relative intensity of mentioned peaks are all stable at comparatively high value (between 1.5% and 5%), which may be affected by sample, instrument, testing condition, etc. to be fluctuated, and the repeatability of these peaks are lower than that of the above mentioned characteristic peaks.

Allisartan isoproxil polymorph mentioned in the present invention has diffraction peaks at diffraction angle (2θ) of 9.6, 10.0, 13.2, 14.4, 15.9, 18.2, 24.5, 25.0, 28.9, 29.9, 30.3 and 35.1 in the X-ray powder diffraction spectra (XRD spectra) and the error range is ±0.2°. The relative intensity of mentioned peaks are at comparatively lower value (below 1.5%), which are prone to be affected by sample, instrument, testing condition, etc. to fluctuate obviously, so they have the lowest repeatability.

Through repeated tests on samples obtained and comparison between XRD spectras of the samples, it is found that all the repeated tests have the following diffraction peaks, and the error range of 2θ and d(Å) is ±0.2:

| No. | 2θ(°) | Interplanar spacing d(Å) |
|---|---|---|
| 1 | 6.9 | 12.8 |
| 2 | 8.0 | 11.1 |
| 3 | 9.6 | 9.2 |
| 4 | 10.0 | 8.9 |
| 5 | 13.2 | 6.7 |
| 6 | 13.8 | 6.4 |
| 7 | 14.4 | 6.2 |
| 8 | 15.9 | 5.6 |
| 9 | 17.4 | 5.1 |
| 10 | 18.2 | 4.9 |
| 11 | 18.9 | 4.7 |
| 12 | 19.3 | 4.6 |
| 13 | 19.6 | 4.5 |
| 14 | 20.1 | 4.4 |
| 15 | 21.1 | 4.2 |
| 16 | 21.5 | 4.1 |
| 17 | 22.2 | 4.0 |
| 18 | 22.6 | 3.9 |
| 19 | 24.0 | 3.7 |
| 20 | 24.5 | 3.6 |
| 21 | 25.0 | 3.56 |
| 22 | 27.7 | 3.2 |
| 23 | 28.9 | 3.1 |
| 24 | 29.9 | 2.99 |
| 25 | 30.3 | 2.9 |
| 26 | 32.1 | 2.8 |
| 27 | 34.8 | 2.6 |
| 28 | 35.1 | 2.55 |

Figure 3:
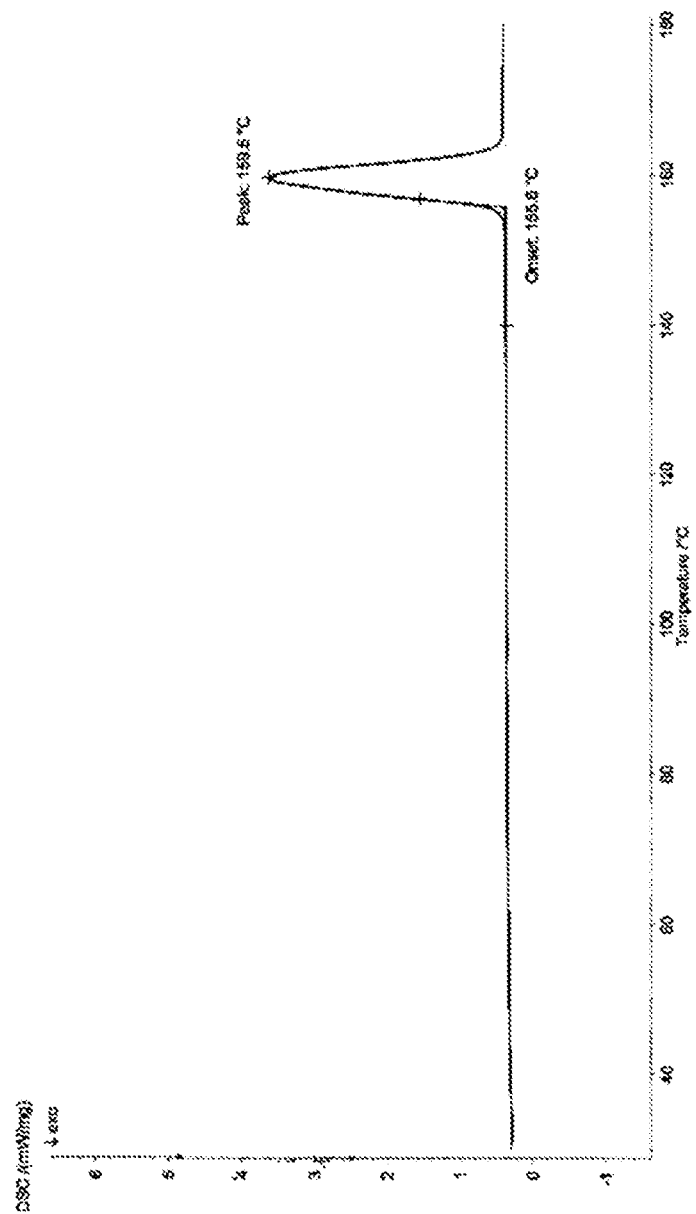

The DSC spectrum of the mentioned allisartan isoproxil polymorph is shown as FIG. 3. Specially, the spectrum shows endothermic peak at 159±3° C.

Figure 4:
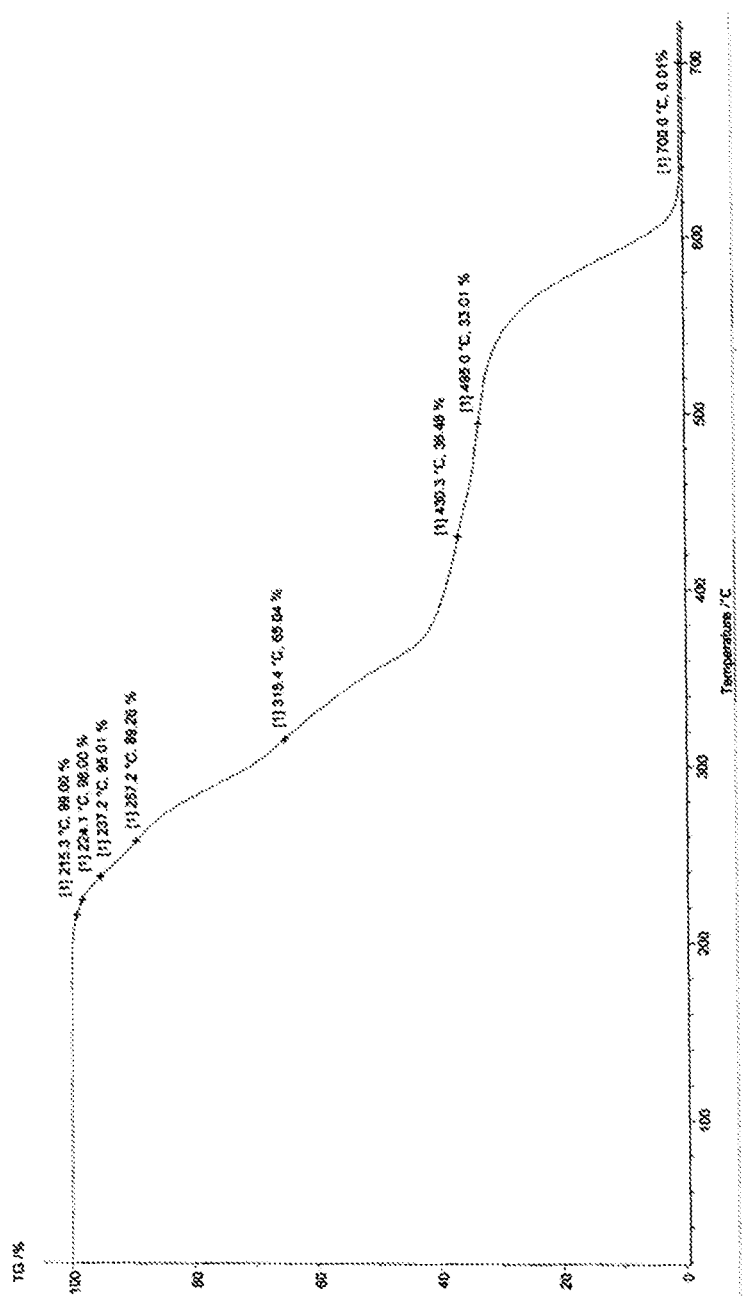

The TG spectrum of the mentioned allisartan isoproxil polymorph is shown as FIG. 4. It can be seen that the mentioned allisartan isoproxil polymorph doesn't contain crystallization solvent, so it is non-solvated.

Another object of the present invention is to provide a preparation method of allisartan isoproxil polymorph by using mixed solvent; more specifically, the mentioned preparation method comprises the following steps:
1) Dissolve allisartan isoproxil in the mixed solvent composed of solvent A and solvent B under heating;
2) Crystal is precipitated by temperature reduction;
3) Cool the solvent system slowly to 0~15° C. for further crystallization;
4) Obtain allisartan isoproxil crystal through separation and drying.

In the mentioned step 1), the amount of solvent should be used are based on that can dissolve clarification; solvent A is selected from the group consisting of C3-C4 alcohols or their corresponding acetates, preferably 2-butanol, isopropyl alcohol, isopropyl acetate; solvent B is selected from the group consisting of C5-C7 chain alkanes, preferably n-heptane; the volume ratio of mentioned solvent A to solvent B is 0.5~1.5:1.

Compared with the allisartan isoproxil polymorph disclosed in available technologies, polymorph in the present invention shows better flowability, non-electrostatic phenomenon, makes product more convenient during weighing or transferring, and also effectively shortens the mixing time with excipients.

In the stability study, we are surprised to find that the mentioned polymorph shows characteristics of high stability; specifically, the mentioned polymorph remains stable in high temperature, high humidity and light condition during the study of influence factors, no obvious degradation happens, which can meet the requirements of storage and subsequent production.

Another purpose of the present invention is to provide a pharmaceutical composition comprising the mentioned allisartan isoproxil polymorph; further, the mentioned pharmaceutical composition contains 0.01% to 99% (W/W) of the mentioned allisartan isoproxil polymorph.

Allisartan isoproxil polymorph provided by the present invention shows good flowability, high stability, etc., so it is more suitable for further preparation of pharmaceutical composition in many aspects, e.g. uniformity and stability of the preparation are superior to those disclosed in available technologies. Specifically, the mentioned pharmaceutical compositions contain but not limited to tablet, capsule, granule, powder, suppository, etc.; preferably, the mentioned pharmaceutical composition is tablet, which includes mentioned Allisartan isoproxil polymorph, disintegrant, binder, filler and lubricant. The disintegrant, binder, filler and lubricant are commonly used pharmaceutical excipients in this field. Specifically, the disintegrant can be selected from one or mixture of more than one of croscarmellose sodium, dry starch, cross-linked povidone, sodium carboxymethyl starch, low substituted hydroxypropyl cellulose, microcrystalline cellulose, pregelatinized starch, etc.; the quantity of disintegrant can be the same from the known practice in the pharmaceutical field which can achieve the effect of disintegration. The binder is selected from one or mixture of more than one of hydroxypropyl methyl cellulose, hydroxypropyl cellulose, sodium carboxymethyl cellulose, povidone, starch slurry, gelatin, etc. When adding binder, the amount should be that known in the pharmaceutical filed which can achieve the binding effect. The filler is selected from one or mixture of more than one of lactose, mannitol, dextrin, starch, pregelatinized starch, microcrystalline cellulose, calcium sulfate, calcium phosphate, and calcium hydrogen phosphate, etc. The filler amount should be that known in the pharmaceutical field which can achieve the effect of filling. The lubricant is selected from one or mixture of more than one of magnesium stearate, colloidal silicon dioxide, talc powder, PEG, etc. The amount of lubricant is that known in pharmaceutical field which can achieve the lubricating effect.

The mentioned pharmaceutical compositions are prepared by common method in pharmaceutical field. Specifically, the preparation methods include but not limited to dry granulation, wet granulation, direct compression, powder filling, spray drying, FBD (Fluidized Bed Drier) granulation, etc.

Allisartan isoproxil composition mentioned in present patent can be used on treatment of hypertension and its complications. As mentioned earlier, the composition of the present invention is superior to those disclosed in available technologies, therefore, it can achieve better clinical curative effect, but with lower risk. Preferably the mentioned allisartan isoproxil composition can be used for the treatment of mild and moderate primary hypertension. The complications of hypertension refer to diseases caused by hypertension, including heart complications, such as left ventricular hypertrophy, angina, myocardial infarction, heart failure; stroke, such as hemorrhagic stroke, ischemic stroke, hypertensive encephalopathy; hypertensive renal damage, such as slow progression of arteriolar nephrosclerosis, malignant arteriolar nephrosclerosis, chronic renal failure; eye diseases, such as retinal arteriosclerosis, fundus changes.

Compared with the available technologies, the present invention has the following advantages and beneficial effects:

1. Provides a new allisartan isoproxil crystal which is a new polymorph with non-electrostatic phenomenon, good flowability, high stability, and provides one more option for allisartan isoproxil preparation.

2. Provides a crystallization method of allisartan isoproxil polymorph in industrial production, which can produce the mentioned allisartan isoproxil polymorph stably and efficiently.

3. Provides an allisartan isoproxil composition used for treatment hypertension and its complications, which contains allisartan isoproxil polymorph in the present invention, the composition shows high stability, and improves the safety in clinical practice.

BRIEF INTRODUCTION OF THE DRAWINGS

Figure 2:
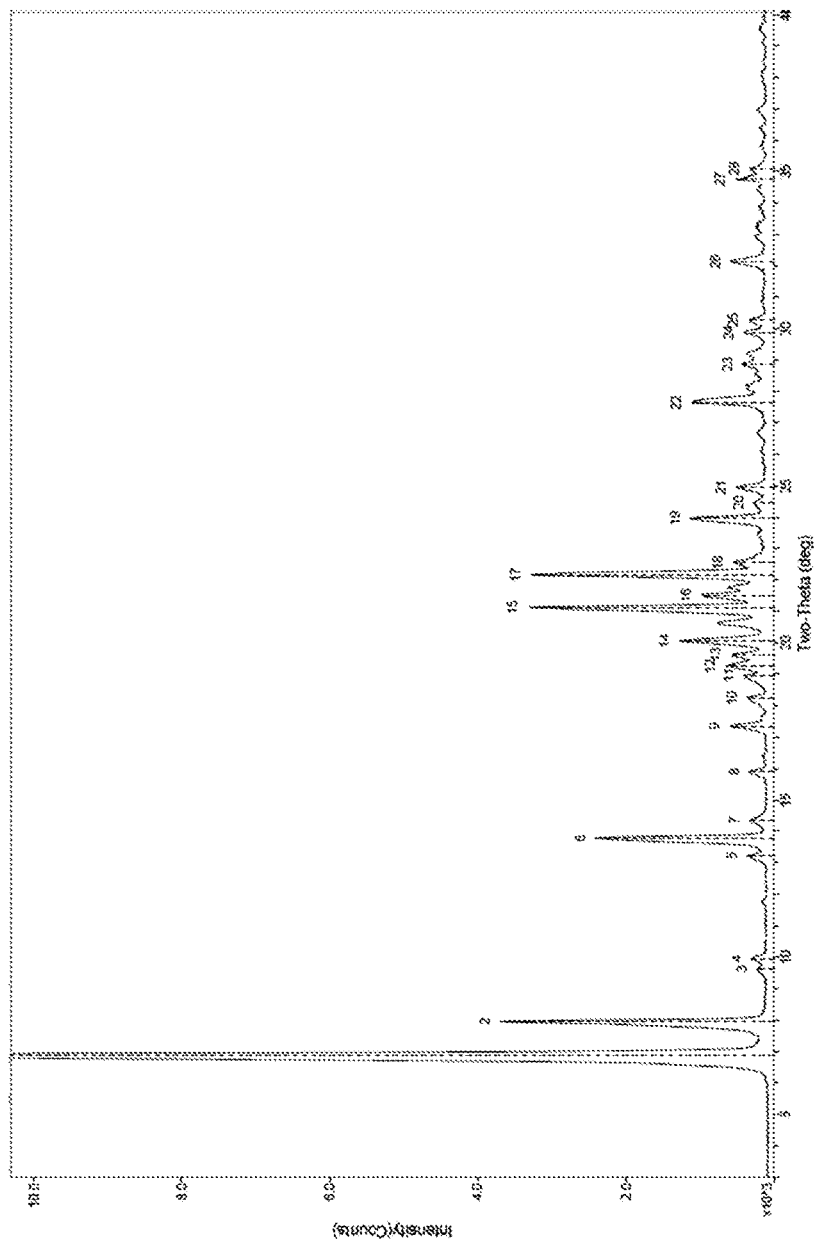
Figure 5:
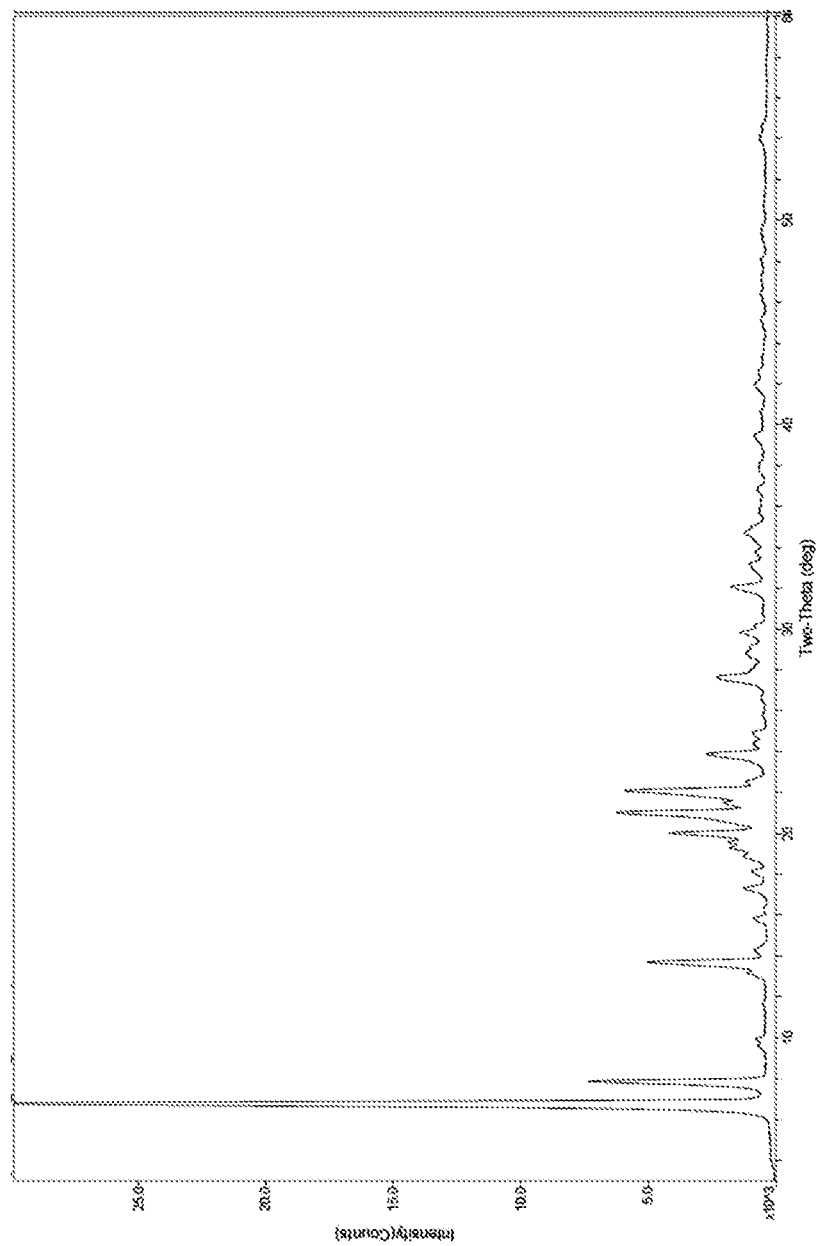
Figure 6:
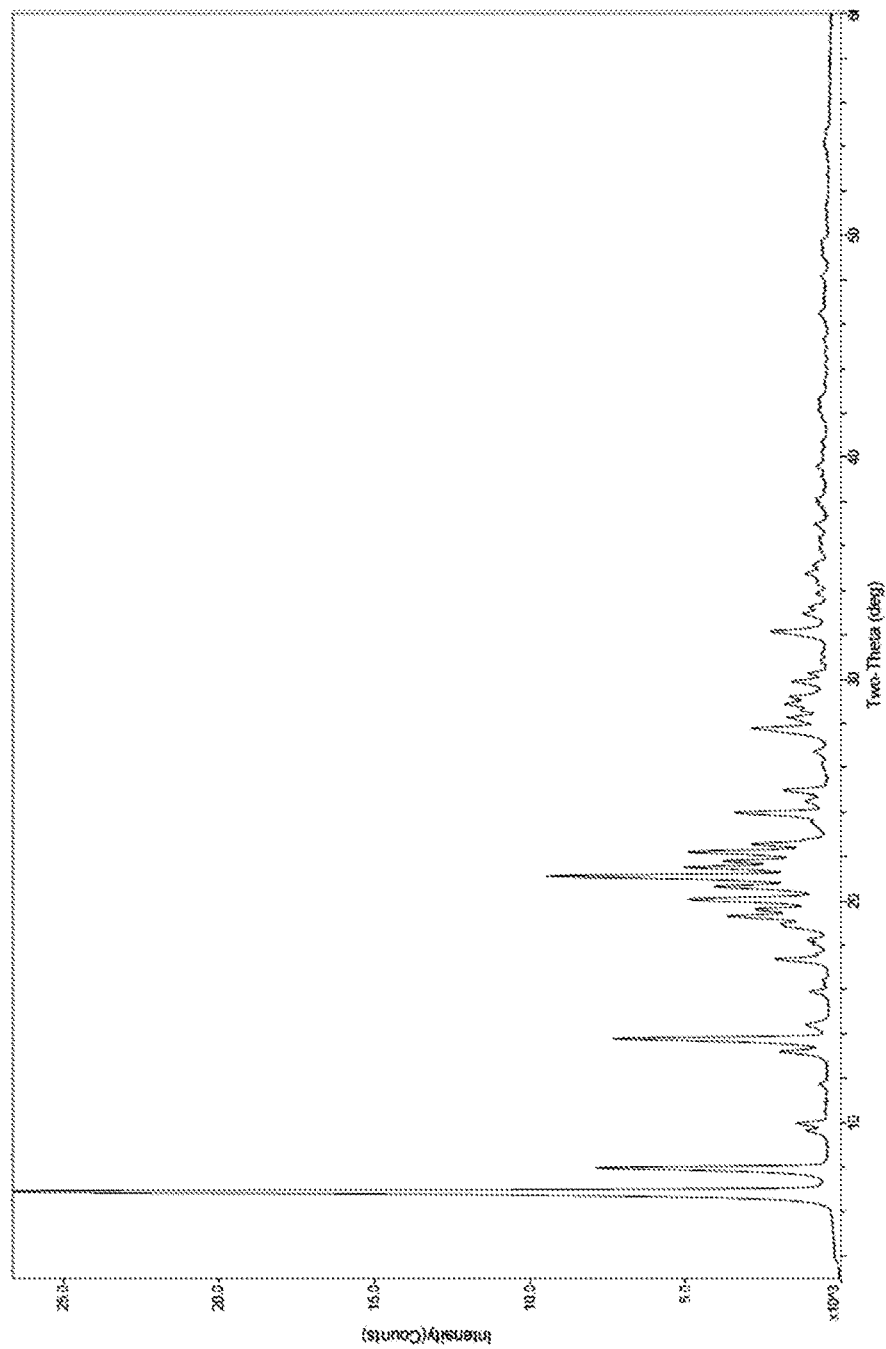
Figure 7:
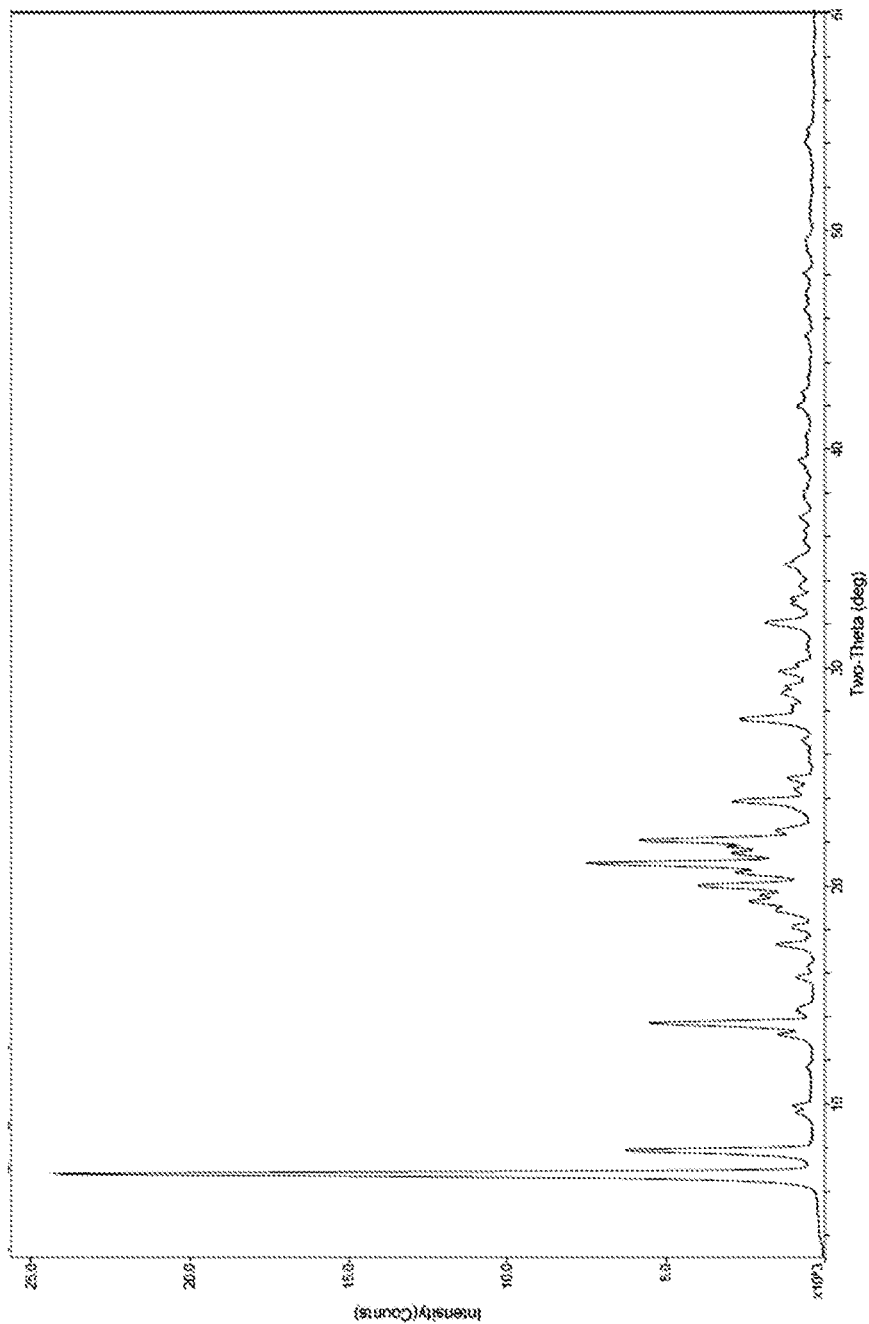

FIG. 1 XRD Spectrum of Allisartan Isoproxil Polymorph Obtained In Example 1;
FIG. 2 Partial Enlarged XRD Spectrum of Allisartan Isoproxil Polymorph Obtained In Example 1;
FIG. 3 DSC Spectrum of Allisartan Isoproxil Polymorph Obtained In Example 1;
FIG. 4 TG Spectrum of Allisartan Isoproxil Polymorph Obtained In Example 1;
FIG. 5 XRD Spectrum of Allisartan Isoproxil Polymorph Obtained In Example 2;
FIG. 6 XRD Spectrum of Allisartan Isoproxil Polymorph Obtained In Example 3; and
FIG. 7 XRD Spectrum of Allisartan Isoproxil Polymorph Obtained In Example 4.

DETAILED DESCRIPTION OF THE EXAMPLES

The present invention is further described in detail in conjunction with the accompanying drawings and examples, but detailed description of the examples are not limited to these.

The following equipment and testing condition used in XRD spectrum:

Testing equipment: Rigaku MiniFlex 600 X ray diffractometer

Test conditions: copper target, voltage 40 KV, electricity current 15 mA, scanning step 0.02°, scanning speed of 5 steps per min, angle range: 3°~60°, Slit: Soller (inc.) 2.5 deg, HIS 10.0 mm, DS 0.625 deg, SS 13.0 mm, Soller (rec.) 2.5 deg, RS 13.0 mm The following equipment and testing condition used in DSC spectrum:

Testing equipment: DSC 204F1 differential scanning calorimeter made by NETZSCH, Germany Test conditions: $N_2$ atmosphere (purity ≥99.99%, 20 ml/min); scan program: room temperature ~180° C.; heating rate: 10° C./min The following equipment and testing condition used in TG spectrum:

Testing equipment: TG209 thermal gravimetric analyzer made by NETZSCH, Germany

Test conditions: air atmosphere, 20 ml/min; scan program: room temperature ~700° C.; heating rate: 10° C./min Raw material, 2-butyl-4-chloro-1-[2'-(1-triphenylmethyl-1H-tetrazol-5-yl)-1,1'-biphenyl-methyl]-imidazole-5-carboxylic acid, 1-[(isopropoxy)-carbonyloxy]methyl ester in Example 1~4 is prepared according to the method disclosed in Example 12 in Chinese patent CN200680000397.8.

Example 1

Weighed 25 g of 2-butyl-4-chloro-1-[2'-(1-triphenylmethyl-1H-tetrazol-5-yl)-1,1'-biphenyl-methyl]-imidazole-5-carboxylic acid, 1-[(isopropoxy)-carbonyloxy]methyl ester into a 500 ml three-necked flask, added 200 ml of methanol. Refluxed for 9 hrs, removed methanol through reduced-pressure distillation, and finally obtained allisartan isoproxil crude.

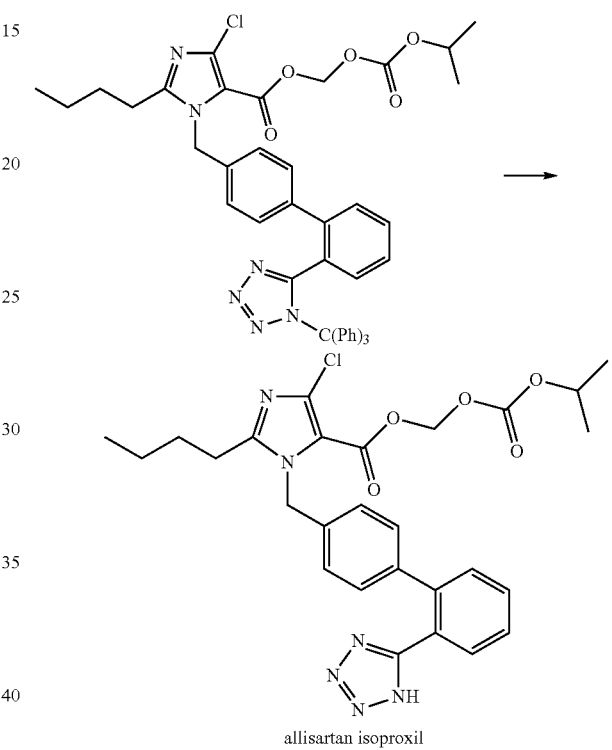

allisartan isoproxil

Added 33 ml of isopropanol and 66 ml of n-heptane in the remainder (allisartan isoproxil crude), heated to 76° C. and stirred for 2 h, then cooled to 60° C. and stirred for 1 h. Cooled the system slowly to 0° C., continued to stir for 3 h. Filtered, and washed the filter cake with n-heptane. After vacuum drying for 8 h at 40° C., obtained 15.3 g of allisartan isoproxil (purity: 99.3%), whose XRD spectrum was shown as FIG. 1. The peak value of the main diffraction peaks were shown in the following table. The DSC spectrum was shown as FIG. 2. Compared with the crystal disclosed, the obtained crystal here does not have obvious electrostatic phenomenon.

| No. | 2θ(°) | Interplanar spacing d(Å) | Relative Intensity (%) |
| --- | --- | --- | --- |
| 1 | 6.9 | 12.8 | 100 |
| 2 | 8.0 | 11.1 | 20 |
| 3 | 9.6 | 9.2 | 0.6 |
| 4 | 10.0 | 8.9 | 1.1 |
| 5 | 13.2 | 6.7 | 1.3 |
| 6 | 13.8 | 6.4 | 13 |
| 7 | 14.4 | 6.2 | 1.0 |
| 8 | 15.9 | 5.6 | 1.3 |

-continued

| No. | 2θ(°) | Interplanar spacing d(Å) | Relative Intensity (%) |
| --- | --- | --- | --- |
| 9 | 17.4 | 5.1 | 2.7 |
| 10 | 18.2 | 4.9 | 1.3 |
| 11 | 18.9 | 4.7 | 1.5 |
| 12 | 19.3 | 4.6 | 2.7 |
| 13 | 19.6 | 4.5 | 2.1 |
| 14 | 20.1 | 4.4 | 5.8 |
| 15 | 20.6 | 4.3 | 2.6 |
| 16 | 21.1 | 4.2 | 17 |
| 17 | 21.5 | 4.1 | 3.4 |
| 18 | 21.7 | 4.08 | 1.7 |
| 19 | 22.2 | 4.0 | 17 |
| 20 | 22.6 | 3.9 | 2.2 |
| 21 | 24.0 | 3.7 | 5.4 |
| 22 | 24.5 | 3.6 | 0.6 |
| 23 | 25.0 | 3.56 | 2.0 |
| 24 | 27.7 | 3.2 | 5.3 |
| 25 | 28.2 | 3.16 | 1.1 |
| 26 | 28.9 | 3.1 | 1.3 |
| 27 | 29.2 | 3.05 | 1.1 |
| 28 | 29.9 | 2.99 | 1.4 |
| 29 | 30.3 | 2.9 | 1.1 |
| 30 | 32.1 | 2.8 | 2.5 |
| 31 | 34.8 | 2.6 | 2.2 |
| 32 | 35.1 | 2.55 | 1.2 |

Example 2

Weighed 25 g of 2-butyl-4-chloro-1-[2'-(1-triphenylm-ethyl-1H-tetrazol-5-yl)-1,1'-biphenyl-methyl]-imidazole-5-carboxylic acid, 1-[(isopropoxy)-carbonyloxy]methyl ester into a 500 ml three-necked flask, added 200 ml of methanol, then refluxed for 9 hrs. Removed methanol through reduced-pressure distillation, and finally obtained allisartan isoproxil crude.

Added 60 ml of isopropanol in the remainder (allisartan isoproxil crude), refluxed to dissolved clarification, and added 50 ml of n-heptane; after dissolved clarification again, cooled to 40° C. under stirring, and crystal was starting to separate out; continued to stir for 1 h, cooled the system slowly to 10° C. then stirred for 1 h. Filtered, and washed the filter cake with n-heptane. After vacuum drying for 8 h at 40° C., obtained 14.3 g of allisartan isoproxil (purity: 98.6%), whose XRD spectrum was shown as FIG. 5. The peak value of the main diffraction peaks were shown in the following table. The DSC spectrum was basically the same as shown in Example 1.

| No. | 2θ(°) | Interplanar spacing d(Å) | Relative Intensity (%) |
| --- | --- | --- | --- |
| 1 | 6.8 | 13.0 | 100 |
| 2 | 7.9 | 11.2 | 21 |
| 3 | 9.6 | 9.2 | 0.9 |
| 4 | 9.9 | 8.9 | 1.2 |
| 5 | 13.2 | 6.7 | 1.8 |
| 6 | 13.7 | 6.5 | 14 |
| 7 | 14.3 | 6.2 | 1.0 |
| 8 | 15.8 | 5.6 | 1.6 |
| 9 | 17.3 | 5.1 | 2.5 |
| 10 | 18.1 | 4.9 | 1.5 |
| 11 | 18.9 | 4.7 | 2.3 |
| 12 | 19.3 | 4.6 | 4.0 |
| 13 | 19.6 | 4.5 | 3.0 |
| 14 | 20.0 | 4.4 | 9.5 |
| 15 | 21.0 | 4.2 | 15 |
| 16 | 21.5 | 4.1 | 2.0 |
| 17 | 22.1 | 4.0 | 17 |
| 18 | 22.5 | 3.9 | 2.2 |
| 19 | 23.9 | 3.7 | 6.5 |
| 20 | 24.4 | 3.6 | 0.7 |
| 21 | 24.9 | 3.6 | 1.1 |
| 22 | 27.7 | 3.2 | 5.3 |
| 23 | 28.9 | 3.1 | 1.5 |
| 24 | 29.8 | 3.0 | 2.5 |
| 25 | 30.2 | 2.96 | 1.0 |
| 26 | 32.1 | 2.8 | 3.7 |
| 27 | 32.9 | 2.7 | 1.2 |
| 28 | 33.2 | 2.69 | 1.3 |
| 29 | 34.7 | 2.6 | 2.1 |
| 30 | 35.1 | 2.56 | 1.3 |

Example 3

Weighed 25 g of 2-butyl-4-chloro-1-[2'-(1-triphenylm-ethyl-1H-tetrazol-5-yl)-1,1'-biphenyl-methyl]-imidazole-5-carboxylic acid, 1-[(isopropoxy)-carbonyloxy] methyl ester, put in a 500 ml three-necked flask, then added 200 ml of methanol. Refluxed for 9 hrs, removed methanol through reduced-pressure distillation, and finally obtained allisartan isoproxil crude. Added 100 ml of isopropyl acetate in the remainder (allisartan isoproxil crude), refluxed to dissolved clarification, then added 100 ml of n-heptane. After dissolved clarification again, cooled to 60° C. under stirring, and crystal was starting to separate out; continued to stir for 3 h, cooled the system slowly to 10° C., then stirred for 12 h. Filtered and washed the filter cake with n-heptane. After vacuum drying 8 h at 40° C., obtained 14.2 g of allisartan isoproxil (purity: 98.5%), whose XRD spectrum was shown as FIG. 6. The peak value of the main diffraction peaks were shown in the following table. The DSC spectrum was basically the same as shown in Example 1.

| No. | 2θ(°) | Interplanar spacing d(Å) | Relative Intensity (%) |
| --- | --- | --- | --- |
| 1 | 6.9 | 12.8 | 100 |
| 2 | 8.0 | 11.1 | 23 |
| 3 | 9.6 | 9.2 | 1.9 |
| 4 | 10.0 | 8.8 | 3.2 |
| 5 | 13.2 | 6.7 | 4.6 |
| 6 | 13.8 | 6.4 | 22 |
| 7 | 14.4 | 6.1 | 2.0 |
| 8 | 15.9 | 5.6 | 2.0 |
| 9 | 17.4 | 5.1 | 5.2 |
| 10 | 18.0 | 4.9 | 1.1 |
| 11 | 18.2 | 4.86 | 1.6 |
| 12 | 18.9 | 4.68 | 4.3 |
| 13 | 19.3 | 4.6 | 10 |
| 14 | 19.6 | 4.5 | 5.7 |
| 15 | 20.1 | 4.4 | 12 |
| 16 | 20.6 | 4.3 | 7.0 |
| 17 | 21.1 | 4.2 | 26 |
| 18 | 21.5 | 4.1 | 10 |
| 19 | 21.8 | 4.07 | 9.1 |
| 20 | 22.2 | 4.0 | 14 |
| 21 | 22.6 | 3.9 | 7.4 |
| 22 | 23.5 | 3.8 | 1.1 |
| 23 | 24.0 | 3.7 | 8.7 |
| 24 | 24.5 | 3.6 | 1.5 |
| 25 | 25.0 | 3.56 | 4.2 |
| 26 | 26.7 | 3.3 | 1.2 |
| 27 | 27.8 | 3.2 | 7.0 |
| 28 | 28.3 | 3.16 | 2.7 |
| 29 | 28.6 | 3.1 | 1.2 |
| 30 | 28.9 | 3.09 | 3.1 |
| 31 | 29.2 | 3.06 | 2.8 |

| No. | 2θ(°) | Interplanar spacing d(Å) | Relative Intensity (%) |
|---|---|---|---|
| 32 | 29.9 | 3.0 | 3.1 |
| 33 | 30.3 | 2.9 | 1.7 |
| 34 | 32.2 | 2.8 | 5.5 |
| 35 | 33.0 | 2.7 | 2.1 |
| 36 | 33.3 | 2.69 | 1.4 |
| 37 | 34.7 | 2.6 | 1.9 |
| 38 | 35.1 | 2.55 | 1.2 |

Example 4

Weighed 25 g of 2-butyl-4-chloro-1-[2'-(1-allisartan isoproxil-1H-tetrazol-5-yl)-1,1'-biphenyl-methyl]-imidazole-5-carboxylic acid, 1-[(isopropoxy)-carbonyloxy]methyl ester, put in a 500 ml three-necked flask, then added 200 ml of methanol. Refluxed for 9 hrs, removed methanol through reduced-pressure distillation, and finally obtained allisartan isoproxil crude.

Added 52 ml of 2-butanol in the remainder (allisartan isoproxil crude), refluxed to dissolved clarification, and added 40 ml of n-heptane; After dissolved clarification again, cooled to 55° C. with stirring, and crystal was starting to separate out; continued to stir for 1 h, cooled the system slowly to 10° C., then stirred for 12 h. Filtered and washed the filter cake with n-heptane. After vacuum drying 12 h at 45° C., obtained 14.6 g of allisartan isoproxil (purity 97.8%), whose XRD spectrum was shown as FIG. 7. The peak value of the main diffraction peaks were shown in the following table. The DSC spectrum was basically the same as shown in Example 1.

| No. | 2θ(°) | Interplanar spacing d(Å) | Relative Intensity (%) |
|---|---|---|---|
| 1 | 6.8 | 13.0 | 100 |
| 2 | 7.9 | 11.1 | 24 |
| 3 | 9.6 | 9.2 | 1.9 |
| 4 | 10.0 | 8.9 | 2.5 |
| 5 | 13.2 | 6.7 | 4.0 |
| 6 | 13.7 | 6.5 | 21 |
| 7 | 14.3 | 6.2 | 1.5 |
| 8 | 15.8 | 5.6 | 2.2 |
| 9 | 17.3 | 5.1 | 4.6 |
| 10 | 18.2 | 4.9 | 2.1 |
| 11 | 18.9 | 4.7 | 4.2 |
| 12 | 19.3 | 4.6 | 7.8 |
| 13 | 19.6 | 4.5 | 4.7 |
| 14 | 20.0 | 4.4 | 12 |
| 15 | 20.6 | 4.3 | 6.0 |
| 16 | 21.0 | 4.2 | 24 |
| 17 | 21.5 | 4.1 | 4.5 |
| 18 | 21.8 | 4.07 | 9.5 |
| 19 | 22.1 | 4.0 | 22 |
| 20 | 22.5 | 3.9 | 4.2 |
| 21 | 23.9 | 3.7 | 9.6 |
| 22 | 24.5 | 3.6 | 1.1 |
| 23 | 24.9 | 3.57 | 2.5 |
| 24 | 26.7 | 3.3 | 1.0 |
| 25 | 27.7 | 3.2 | 8.5 |
| 26 | 28.2 | 3.15 | 1.3 |
| 27 | 28.9 | 3.1 | 2.6 |
| 28 | 29.2 | 3.06 | 2.3 |
| 29 | 29.8 | 3.0 | 3.4 |
| 30 | 30.2 | 2.95 | 1.5 |
| 31 | 32.1 | 2.8 | 5.6 |
| 32 | 32.9 | 2.72 | 1.9 |
| 33 | 33.2 | 2.70 | 2.1 |
| 34 | 34.3 | 2.6 | 1.1 |
| 35 | 34.7 | 2.58 | 2.9 |
| 36 | 35.0 | 2.56 | 1.6 |

Example 5

Data of Example 1~4 Were Summarized and Analyzed.

It is well known in the field that, in the X-ray diffraction study on polymorph, high stability of strong diffraction peaks are less influenced by instruments and testing conditions, most of which are characteristic peaks; for low intensity diffraction peaks, the lower intensity the peaks are, the more easily to be influenced by sample, instrument and testing conditions, the less probable to appear repeatedly in corresponding spectrums.

Specifically, by statistical analysis, it was found that allisartan isoproxil polymorph mentioned in the present invention had diffraction peaks at diffraction angles (2θ) of 6.9, 8.0, 13.8, 20.1, 21.1, 22.2, 24.0, and 27.7 in the XRD spectrum and the error range was ±0.2°. The mentioned peaks were stable at high intensive (5% and above 5%), and these peaks which could appear in repeated tests belonged to the characteristic peaks of new polymorph in the present invention.

Allisartan isoproxil polymorph mentioned in the present invention had diffraction peaks at diffraction angles (2θ) of 17.4, 18.9, 19.3, 19.6, 21.5, 22.6, 32.1 and 34.8 in the XRD spectrum and the error range was ±0.2°. The relative intensity of mentioned peaks were all stable at comparable higher value (between 1.5% and 5%), which might be affected by sample, instrument, testing condition, etc. to fluctuate and the repeatability were lower than that of the above mentioned characteristic peaks.

Allisartan isoproxil polymorph mentioned in the present invention has diffraction peaks at diffraction angles (2θ) of 9.6, 10.0, 13.2, 14.4, 15.9, 18.2, 24.5, 25.0, 28.9, 29.9, 30.3 and 35.1 in the XRD spectrum the error range was ±0.2°. The relative intensity of mentioned peaks were all stable at lower value (below 1.5%), which were prone to be affected by sample, instrument, testing condition, etc. to fluctuate obviously, so they had the lowest repeatability.

More specifically, through comparison of the XRD spectra of samples obtained in Example 1~4, it was found that all the repeated tests had the following diffraction peaks, and the error range of 2θ and d(Å) is ±0.2:

| No. | 2θ(°) | Interplanar spacing d(Å) |
|---|---|---|
| 1 | 6.9 | 12.8 |
| 2 | 8.0 | 11.1 |
| 3 | 9.6 | 9.2 |
| 4 | 10.0 | 8.9 |
| 5 | 13.2 | 6.7 |
| 6 | 13.8 | 6.4 |
| 7 | 14.4 | 6.2 |
| 8 | 15.9 | 5.6 |
| 9 | 17.4 | 5.1 |
| 10 | 18.2 | 4.9 |
| 11 | 18.9 | 4.7 |
| 12 | 19.3 | 4.6 |
| 13 | 19.6 | 4.5 |
| 14 | 20.1 | 4.4 |
| 15 | 21.1 | 4.2 |
| 16 | 21.5 | 4.1 |

-continued

| No. | 2θ(°) | Interplanar spacing d(Å) |
|---|---|---|
| 17 | 22.2 | 4.0 |
| 18 | 22.6 | 3.9 |
| 19 | 24.0 | 3.7 |
| 20 | 24.5 | 3.6 |
| 21 | 25.0 | 3.56 |
| 22 | 27.7 | 3.2 |
| 23 | 28.9 | 3.1 |
| 24 | 29.9 | 2.99 |
| 25 | 30.3 | 2.9 |
| 26 | 32.1 | 2.8 |
| 27 | 34.8 | 2.6 |
| 28 | 35.1 | 2.55 |

Example 6

Repeated the method of patent CN200710094131.0 to obtain fine loose allisartan isoproxil powder (referred to as literature crystal), measured the response angle by fixed funnel method. Determined the bulk density by cylinder knocking method, and the results were shown in the following table:

| Sample | Repose angle (°) | Bulk density (g/ml) |
|---|---|---|
| Example 1 | 34-36 | 0.75 |
| Example 2 | 35-37 | 0.73 |
| Example 3 | 33-35 | 0.77 |
| Example 4 | 35-38 | 0.77 |
| Literature crystal | 48-53 | 0.51 |

It could be seen from the above data, allisartan isoproxil polymorph prepared in the present invention had better flowability than that disclosed in patent CN200710094131.0, reflected as angle of repose of new polymorph was less than that of patent literature crystal, and its bulk density was greater than that of patent literature crystal.

Example 7

Stability study on the mentioned polymorph in Example 1 was performed in high temperature, high humidity and light conditions to study the influence factors. The results were in the following table:

| Time (day) | Weight gained (%) | Sum of impurities (%) |
|---|---|---|
| High temperature test results (60° C.) | | |
| 0 | 0 | 0.39 |
| 5 | 0 | 0.39 |
| 10 | 0 | 0.39 |
| High humidity test results (25° C., RH 92.5%, saturated solution of potassium nitrate) | | |
| 0 | 0 | 0.39 |
| 5 | 0 | 0.37 |
| 10 | 0 | 0.38 |
| Photostability test result (4500lx ± 500lx) | | |
| 0 | 0 | 0.39 |
| 5 | 0 | 0.37 |
| 10 | 0 | 0.38 |

According to the above photostability study, high humidity and high temperature study, the following conclusions were drawn: allisartan isoproxil polymorph obtained in Example 1 remained stable under various conditions of influence factors, and the purity of the product had no significant change, which met the requirements of storage and subsequent production.

Similarly, allisartan isoproxil polymorph obtained in Example 2, Example 3, and Example 4 had the same result with that of Example 1 on the photostability study, high humidity and high temperature study.

Example 8

Prepare tablets containing allisartan isoproxil polymorph by the method in Example 1.

| Component | Content (g) |
|---|---|
| Allisartan isoproxil | 120 |
| cross-linked povidone | 15 |
| Microcrystalline cellulose | 60 |
| Hydroxypropyl methylcellulose | 10 |
| Microcrystalline cellulose | 45 |
| Magnesium stearate | 2 |
| Total | 252 |
| | Totally, 500 tablets |

Mixed the active ingredient with cross-linked povidone, microcrystalline cellulose and hydroxypropyl methylcellulose completely, and then performed wet granulation. Dried to obtain intragranular granules, mixed the intragranular granules with microcrystalline cellulose and magnesium stearate to obtain the pharmaceutical composition, and then obtained allisartan isoproxil tablets through compression.

The above example is preferable example of the present invention, but its detailed description is not restricted by the example; other change, modification, substitution, combination, simplification not departure from the spirit and principle of the present invention are considered as equivalent replacement, and should be included within the protection of the invention.

The invention claimed is:

1. An allisartan isoproxil polymorph, wherein the allisartan isoproxil polymorph has diffraction peaks at diffraction angles 2θ of 6.9, 8.0, 13.8, 20.1, 21.1, 22.2, 24.0 and 27.7 in an X-ray diffraction (XRD) spectrum and the error range is ±0.20.

2. The allisartan isoproxil polymorph of claim 1, wherein the allisartan isoproxil polymorph has diffraction peaks at diffraction angles 2θ of 17.4, 18.9, 19.3, 19.6, 21.5, 22.6, 32.1 and 34.8 in the XRD spectrum and the error range is ±0.20.

3. The allisartan isoproxil polymorph of claim 1, wherein the allisartan isoproxil polymorph has diffraction peaks at diffraction angles 2θ of 9.6, 10.0, 13.2, 14.4, 15.9, 18.2, 24.5, 25.0, 28.9, 29.9, 30.3 and 35.1 in the XRD spectrum and the error range is ±0.20.

4. The allisartan isoproxil polymorph of claim 1, wherein the allisartan isoproxil polymorph has diffraction peaks at diffraction angles 2θ and d (Å) is ±0.2:

| No. | 2θ(°) | Interplanar spacing d(Å) |
|---|---|---|
| 1 | 6.9 | 12.8 |
| 2 | 8.0 | 11.1 |
| 3 | 9.6 | 9.2 |

-continued

| No. | 2θ(°) | Interplanar spacing d(Å) |
|---|---|---|
| 4 | 10.0 | 8.9 |
| 5 | 13.2 | 6.7 |
| 6 | 13.8 | 6.4 |
| 7 | 14.4 | 6.2 |
| 8 | 15.9 | 5.6 |
| 9 | 17.4 | 5.1 |
| 10 | 18.2 | 4.9 |
| 11 | 18.9 | 4.7 |
| 12 | 19.3 | 4.6 |
| 13 | 19.6 | 4.5 |
| 14 | 20.1 | 4.4 |
| 15 | 21.1 | 4.2 |
| 16 | 21.5 | 4.1 |
| 17 | 22.2 | 4.0 |
| 18 | 22.6 | 3.9 |
| 19 | 24.0 | 3.7 |
| 20 | 24.5 | 3.6 |
| 21 | 25.0 | 3.56 |
| 22 | 27.7 | 3.2 |
| 23 | 28.9 | 3.1 |
| 24 | 29.9 | 2.99 |
| 25 | 30.3 | 2.9 |
| 26 | 32.1 | 2.8 |
| 27 | 34.8 | 2.6 |
| 28 | 35.1 | 2.55. |

5. The allisartan isoproxil polymorph of claim 1, wherein the allisartan isoproxil polymorph has an XRD spectrum as shown in any one of FIG. 1, FIG. 5, FIG. 6, or FIG. 7.

6. The allisartan isoproxil polymorph of claim 1, wherein the allisartan isoproxil polymorph has an endothermic peak at 159±3° C. in a differential scanning calorimetry (DSC) spectrum.

7. The allisartan isoproxil polymorph of claim 1, wherein the allisartan isoproxil polymorph is non-solvated.

8. The allisartan isoproxil polymorph of claim 1, wherein the allisartan isoproxil polymorph has a DSC spectrum as shown in FIG. 3.

9. A method of preparing the allisartan isoproxil polymorph of claim 1, wherein the method comprises the following steps: 1) dissolving allisartan isoproxil in a mixed solvent composed of solvent A and solvent B under heating to obtain a solution; 2) crystal is precipitated by temperature reduction; 3) cooling the solvent system slowly to 0~15° C. for further crystallization; 4) obtaining allisartan isoproxil crystal through separation and drying; wherein in step 1), solvent A is selected from the group consisting of C3-C4 alcohols or their corresponding acetates; solvent B is selected from the group consisting of C5-C7 chain alkanes.

10. The method of claim 9, wherein solvent A is selected from the group consisting of 2-butanol, isopropyl alcohol or isopropyl acetate, solvent B is n-heptane, and the volume ratio of solvent A to solvent B is 0.5~1.5:1.

11. An allisartan isoproxil pharmaceutical composition comprising the allisartan isoproxil polymorph of claim 1.

* * * * *